United States Patent [19]

Green

[11] Patent Number: 4,506,671
[45] Date of Patent: Mar. 26, 1985

[54] APPARATUS FOR APPLYING TWO-PART SURGICAL FASTENERS

[75] Inventor: David T. Green, Norwalk, Conn.

[73] Assignee: United States Surgical Corporation, Norwalk, Conn.

[21] Appl. No.: 480,566

[22] Filed: Mar. 30, 1983

[51] Int. Cl.³ .......................... A61B 17/04; B31B 1/00
[52] U.S. Cl. .................................. 128/334 R; 227/19; 227/DIG. 1; 128/334 C
[58] Field of Search ............... 128/325, 334 R, 334 C, 128/346; 227/DIG. 1 A–DIG. 1 C, 19, 15; 411/469, 475, 476

[56] References Cited

U.S. PATENT DOCUMENTS

| 2,940,451 | 6/1960 | Vogelfanger et al. | 227/DIG. 1 A |
| 3,166,072 | 1/1965 | Sullivan | 128/334 |
| 3,357,296 | 12/1967 | Lefever | 227/DIG. 1 |
| 3,494,533 | 2/1970 | Green et al. | 227/DIG. 1 |
| 4,060,089 | 11/1977 | Noiles | 128/325 |
| 4,198,982 | 4/1980 | Fortner et al. | 128/334 C |
| 4,305,539 | 12/1981 | Korolkov et al. | 227/19 |
| 4,310,115 | 1/1982 | Inoue | 128/334 R |
| 4,402,445 | 9/1983 | Green | 227/19 |

FOREIGN PATENT DOCUMENTS 0906540 2/1982 U.S.S.R. ............................. 334 C/

Primary Examiner—C. Fred Rosenbaum
Assistant Examiner—Gene B. Kartchner
Attorney, Agent, or Firm—Robert R. Jackson; John E. Nathan

[57] ABSTRACT

In apparatus for applying a two-part surgical fastener including a fastener part having at least one prong and a retainer part having an aperture for receiving and retaining the distal end of the prong, the retainer part is initially held securely to the apparatus by contact with a lug extending into the aperture. When the two parts of the fastener are forced together, the distal end of the prong pushes the lug out of the aperture, thereby releasing the retainer part from the apparatus.

21 Claims, 11 Drawing Figures

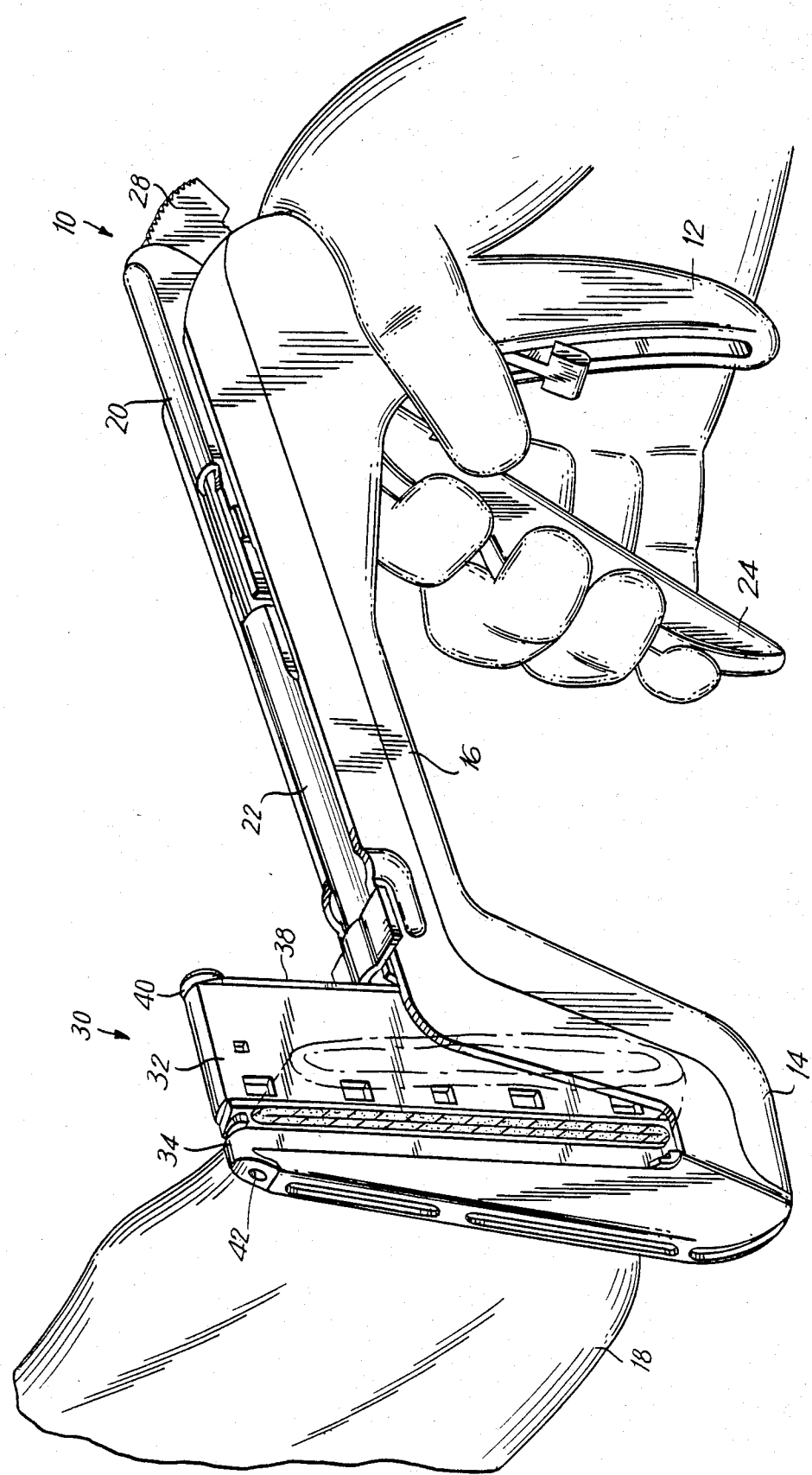

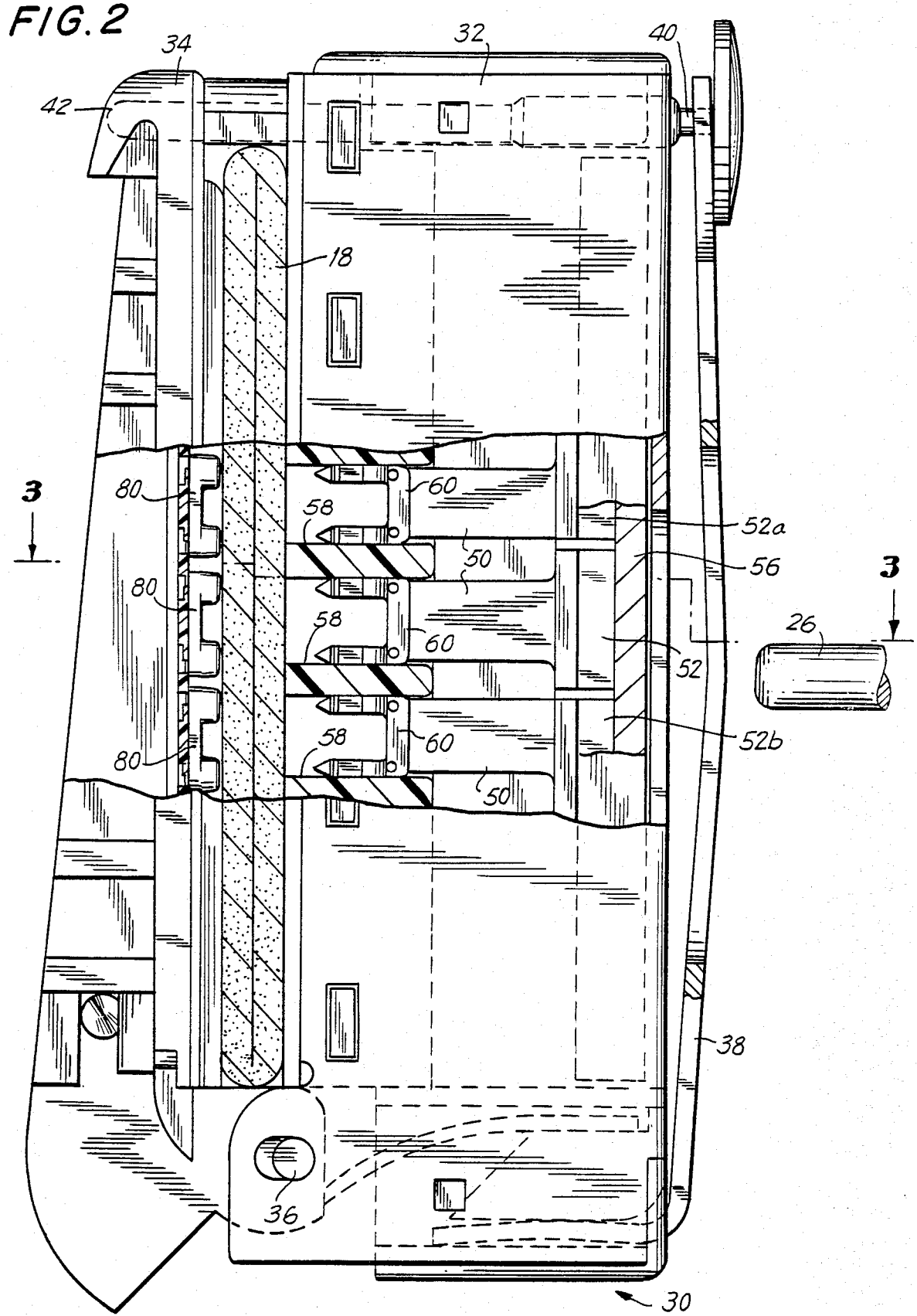

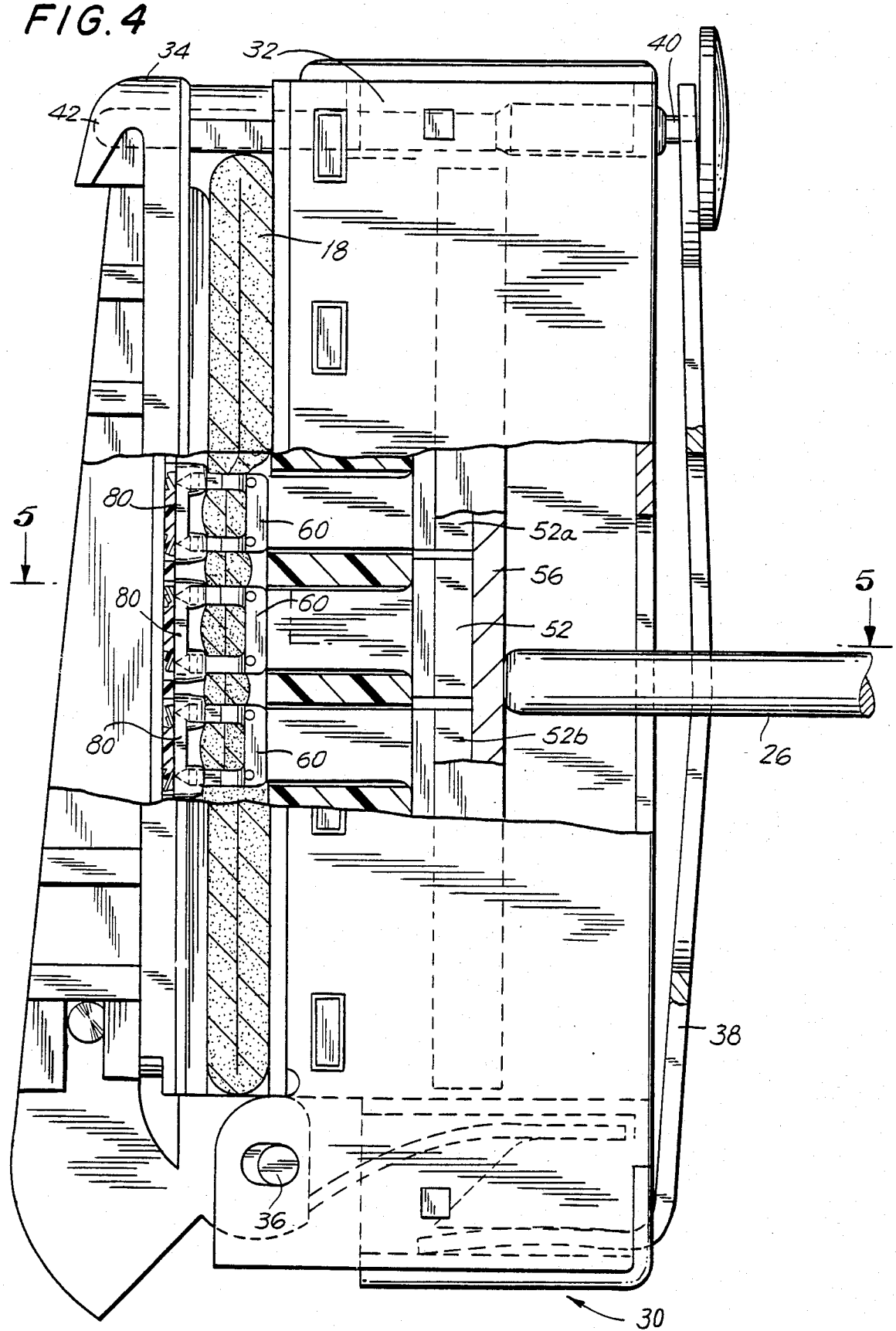

APPARATUS FOR APPLYING TWO-PART SURGICAL FASTENERS

BACKGROUND OF THE INVENTION

This invention relates to surgical fastening apparatus, and more particularly to apparatus for applying surgical fasteners comprising two interlocking parts.

Surgical fasteners have been developed which comprise a fastener part having one or more prongs and a retainer part having a corresponding number of apertures for respectively receiving and engaging the ends of the prongs of the fastener part (see, for example, Noiles U.S. Pat. No. 4,060,089). Both parts of the fastener are typically made of a plastic or plastic-like material which may be biologically absorbable. In use, the fastener and retainer parts are respectively positioned on opposite sides of the tissue to be fastened. The fastener part is then driven toward the tissue so that the prongs pass through the tissue and interlock with the retainer part. The retainer part prevents the prongs from being withdrawn from the tissue.

In applying surgical fasteners of this type it is important for the retainer part to be held securely prior to engaging the fastener part. This is required to prevent the retainer part from becoming loose and possibly lost in the operating site and to assure that each fastener part mates with a retainer part to provide the intended surgical fastening. Once the fastener and retainer parts have interlocked, however, it is equally important for the structure which supports the retainer part to readily release the retainer part so that the fastened tissue can be easily removed from the fastener applying apparatus.

In view of the foregoing, it is an object of this invention to improve and simplify apparatus for applying two-part surgical fasteners of the type described above.

It is a more particular object of this invention to provide apparatus for applying two-part surgical fasteners of the type described above in which the retainer part is held firmly in the apparatus until the two parts of the fastener are joined, after which the retainer parts are released from the apparatus.

SUMMARY OF THE INVENTION

These and other objects of the invention are accomplished in accordance with the principles of the invention by providing a support structure for the retainer part of a two-part surgical fastener, the support structure including means for releasably engaging the retainer part until the prong or prongs of the fastener part have interlocked with the retainer part, at which time the prong or prongs contact the means for releasably engaging the retainer part and cause that means to release the retainer part.

Further features of the invention, its nature and various advantages will be more apparent from the accompanying drawing and the following detailed description of the invention.

BRIEF DESCRIPTION OF THE DRAWING

FIG. 1a shows the permanent actuator and disposable cartridge of this apparatus separate from one another.

FIG. 1b is similar to FIG. 1a but shows the cartridge mounted in the actuator and the apparatus in use.

FIG. 2 is an enlarged view of the cartridge portion of the apparatus shown in FIG. 1b with portions cut away to reveal the interior components.

FIG. 4 is a view similar to FIG. 2 but showing the apparatus after the two parts of the fasteners have been joined.

DETAILED DESCRIPTION OF THE INVENTION

Figure 1A:
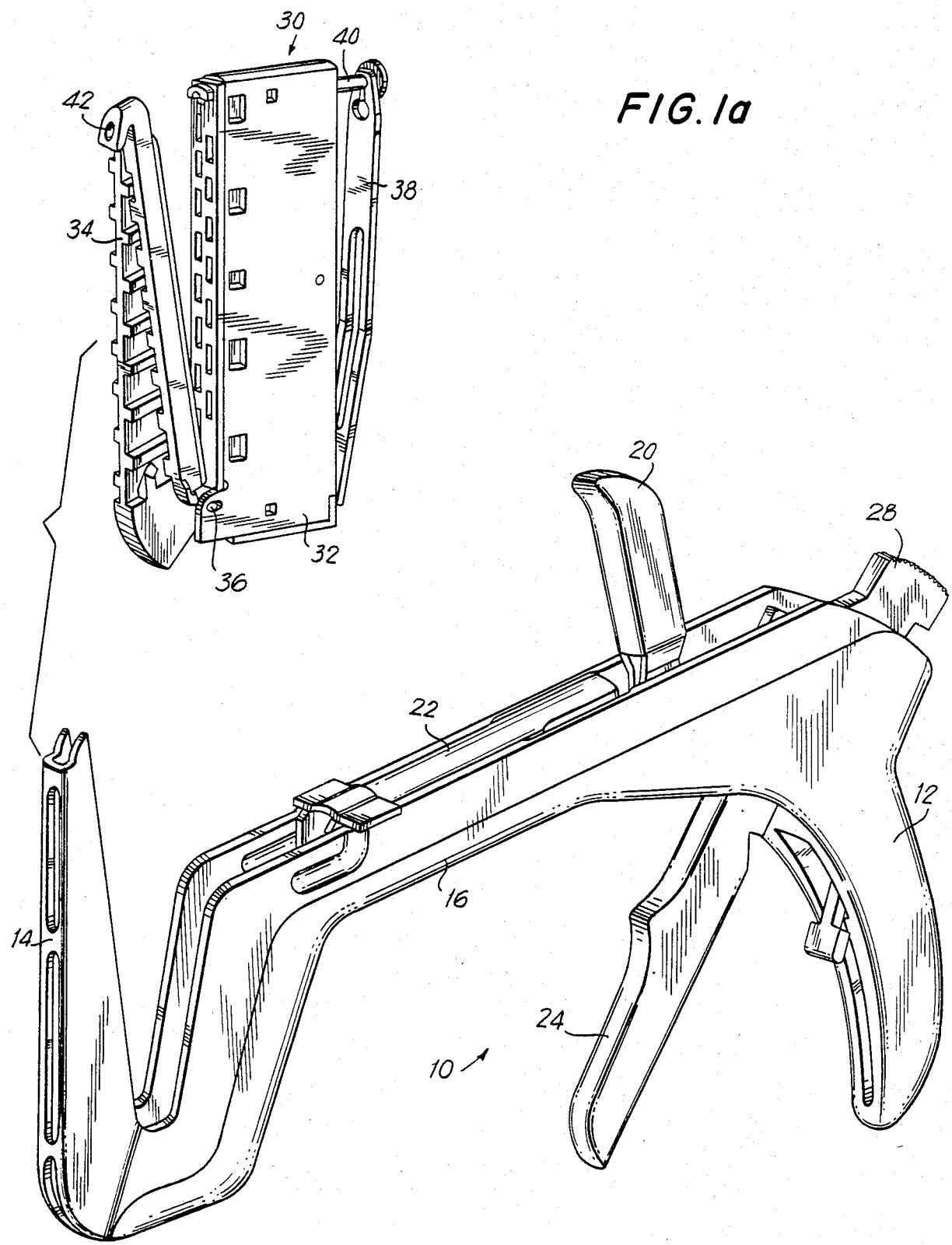
FIG. 1a is a perspective view of an illustrative embodiment of surgical fastener applying apparatus constructed in accordance with this invention.

The surgical fastener applying apparatus shown in the accompanying drawing is only one possible environment of the present invention. As shown in FIG. 1a, this apparatus includes reusable actuator 10 and a replaceable and disposable fastener-carrying cartridge 30. Although not necessary to an understanding of the present invention, full details regarding the construction and operation of actuator 10 are provided in commonly assigned, co-pending Green U.S. patent application Ser. No. 267,080, filed May 26, 1981 now U.S. Pat. No. 4,383,634. Similarly, additional details regarding the construction and operation of a fastener-carrying cartridge similar to cartridge 30 are provided in Green U.S. Pat. No. 4,354,628.

Actuator 10 includes proximal handle 12, distal cartridge holder 14, and intermediate shaft assembly 16. Cartridge 30 includes proximal fastener-holding assembly 32 and distal retainer-holding assembly 34. Assemblies 32 and 34 are pivotally connected to one another by pivotal connection 36. Cartridge 30 slides into actuator 10 as shown in FIG. 1b with retainer-holding assembly 34 firmly but releasably engaged in the distal leg of cartridge holder 14 and with fastener-holding assembly 32 freely movable on pivotal connection 36 between the parallel spaced sides of the proximal leg of cartridge holder 14.

Tissue 18 to be fastened is positioned between fastener-holding assembly 32 and retainer-holding assembly 34. Clamp actuator 20 on actuator 10 is pivoted parallel to shaft assembly 16. This causes clamping assembly 22 to translate toward fastener-holding assembly 32, thereby pivoting the fastener-holding assembly into parallel relationship with retainer-holding assembly 34. As clamping assembly 22 translates toward fastener-holding assembly 32, it first contacts leaf spring 38 which is fixedly mounted near the bottom of fastener-holding assembly 32 and which projects proximally outward from the proximal side of assembly 32. The upper end of leaf spring 38 engages alignment pin 40. When clamping assembly 22 contacts leaf spring 38 as described above, it both pivots assembly 32 toward assembly 34 and substantially flattens leaf spring 38 against the proximal side of assembly 32. This drives alignment pin 40 in the distal direction so that the distal end of pin 40 projects out of assembly 32 and into aperture 42 near the top of assembly 34. This helps to align assemblies 32 and 34 during application of the fasteners to the tissue.

Figure 3:
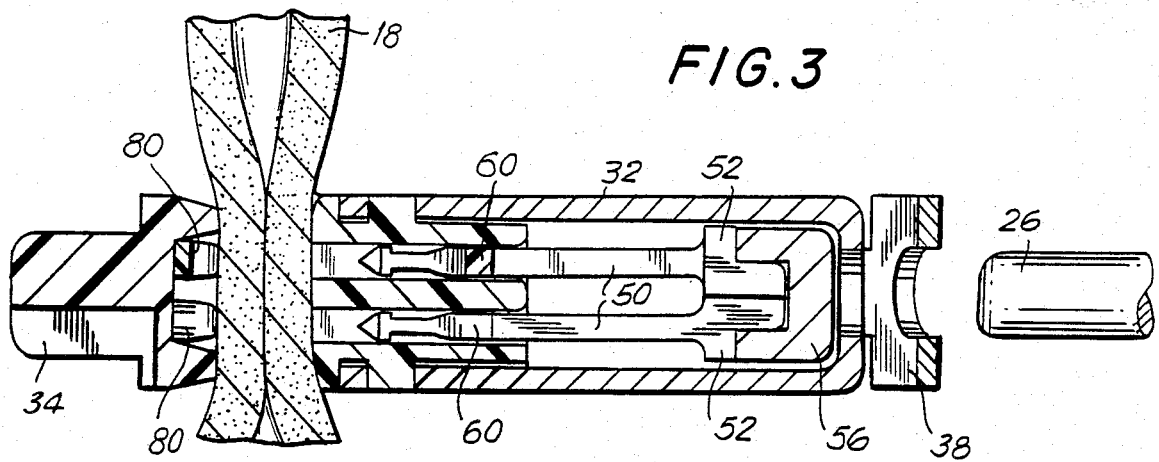
FIG. 3 is a sectional view taken along the line 3—3 in FIG. 2.
Figure 5:
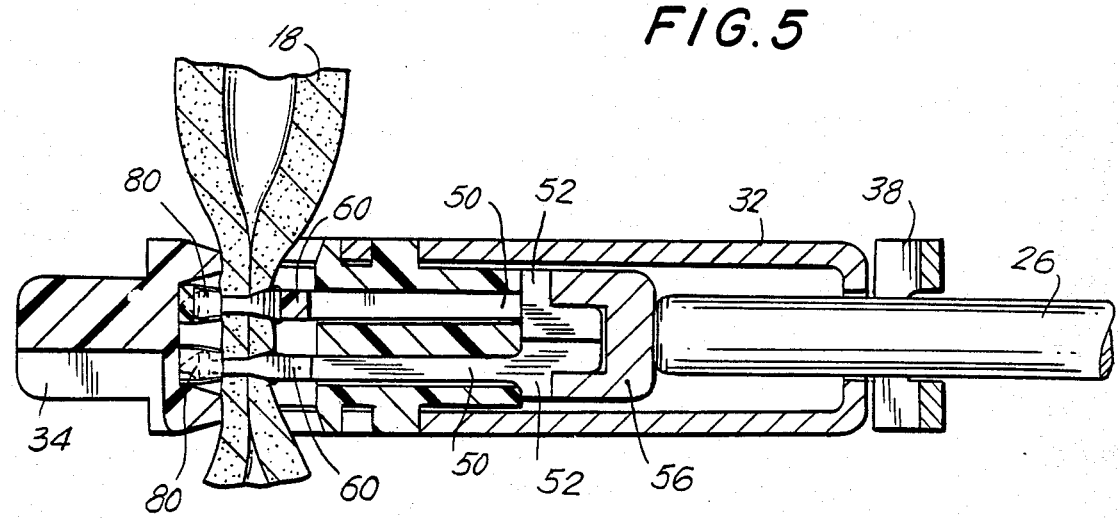
FIG. 5 is a sectional view taken along the line 5—5 in FIG. 4.
Figure 8:
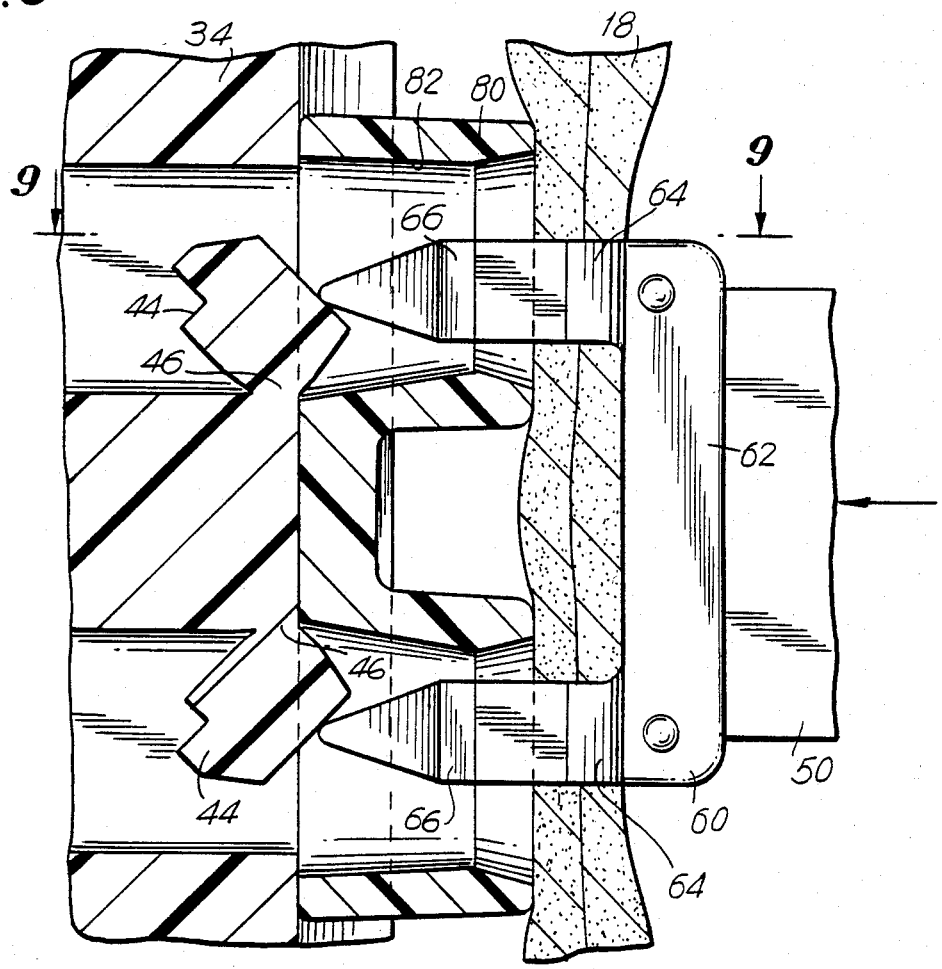
FIG. 8 is a view similar to FIG. 7 but showing the apparatus after the two parts of the fasteners have been joined.

When the tissue 18 has been clamped in the apparatus as described above, fastener actuator 24 is squeezed toward handle 12. This causes elements in assemblies 20 and 22 (the distal-most of these elements being rod 26, FIGS. 2 and 3) to translate in the distal direction. Rod 26 enters the proximal side of fastener-holding assembly 32 as shown in FIGS. 4 and 5 and drives fastener pushers 50 in the distal direction. Each of fastener pushers 50 pushes a U-shaped surgical fastener part 60 in the distal direction. As best seen in FIG. 8, each fastener part 60 includes a base 62 and two parallel prongs 64, each prong being perpendicular to the base at a respective one of the opposite ends of the base.

Figure 9:
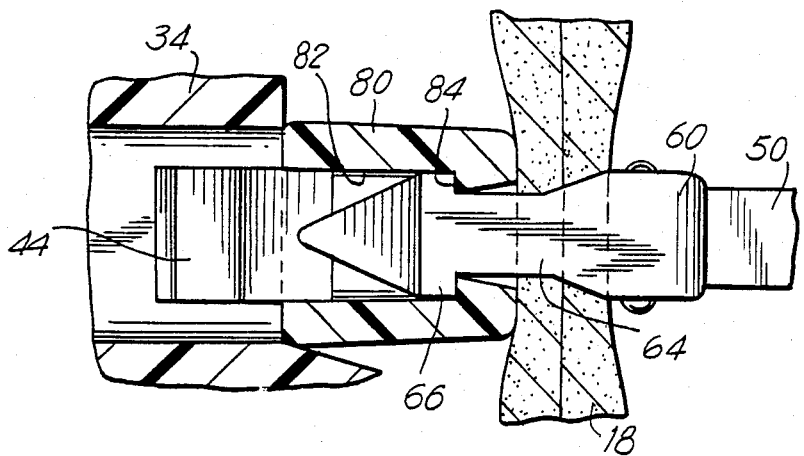
FIG. 9 is a sectional view taken along the line 9—9 in FIG. 8.
Figure 10:
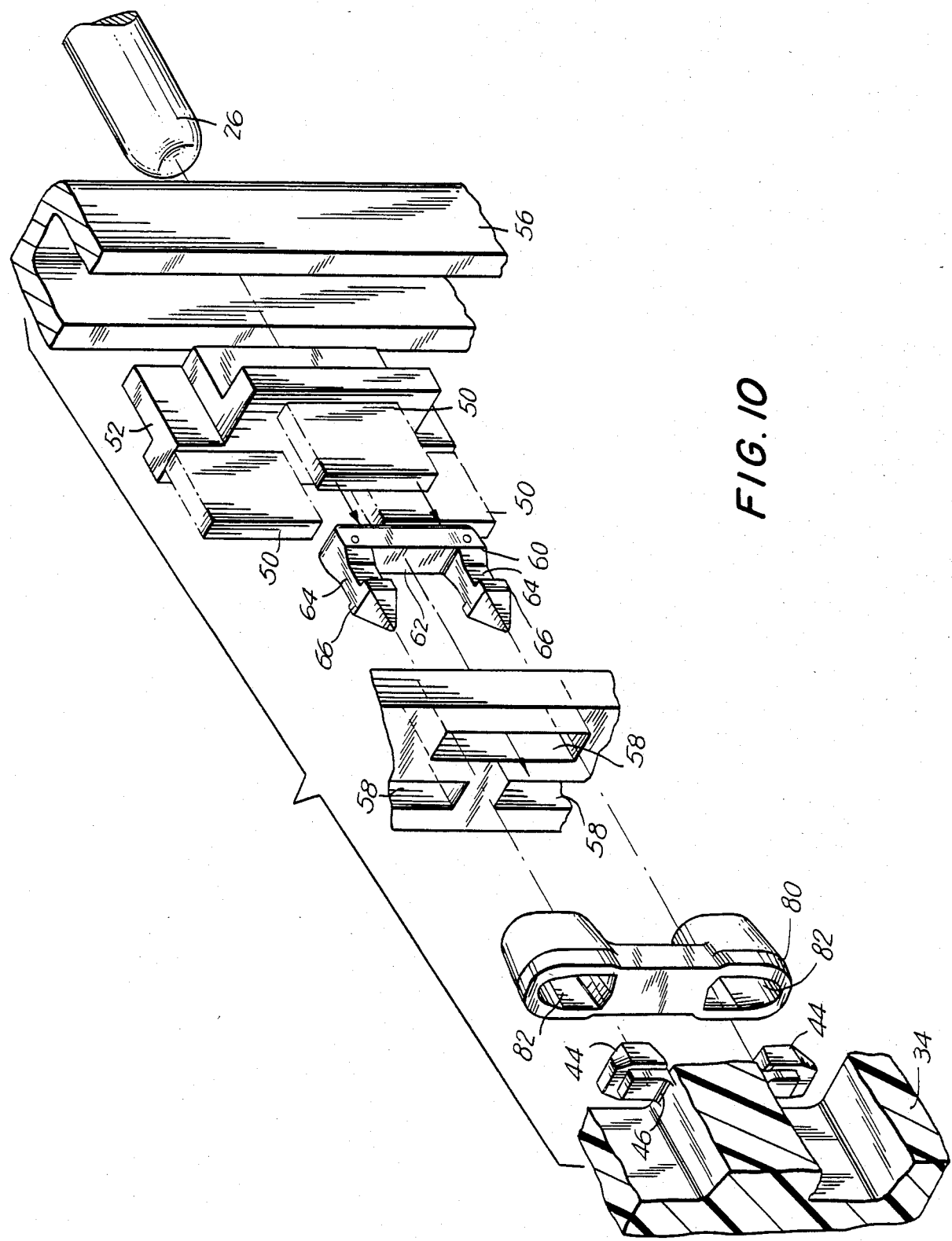
FIG. 10 is a perspective, exploded view of a portion of the apparatus of FIGS. 1-9.

When fastener parts 60 are thus driven in the distal direction, prongs 64 pass through the clamped tissue. After passing through the tissue, the distal end of each prong enters an aligned aperture 82 in a retainer part 80 associated with the fastener part. Retainer parts 80 are supported by and releasably retained in retainer-holding assembly 34 as will be described in greater detail below. As best seen in FIG. 9, the distal end of each prong 64 has an enlarged head 66 which interlocks with interior surfaces 84 of the retainer member aperture to prevent prongs 64 from being withdrawn from the retainer member apertures after the two parts of the fastener have been forced together. Each retainer part 80 thus prevents the associated fastener part 60 from pulling out of the tissue. Fastener part 60 and retainer part 80 cooperate to apply pressure to the fastened tissue as is necessary for such purposes as tissue approximation and hemostasis. In the particular embodiment shown in the drawing, the apparatus applies two parallel rows of fasteners, the rows being longitudinally offset from one another.

When the fasteners have been applied to the tissue as described above, fastener actuator 24 is released. This retracts pin 26 from fastener-holding assembly 32. Clamp actuator 20 is then pivoted out to its original position by depressing release 28. The outward pivoting of clamp actuator 20 retracts clamping assembly 22 and allows cartridge 30 to pivot open. The fastened tissue is removed from cartridge 30. The apparatus is readied for reuse by removing and discarding expended cartridge 30 and reloading actuator 10 with a new cartridge. Between surgical procedures actuator 10 must be cleaned and sterilized, but no such cleaning and sterilization is required for disposable cartridges 30.

Figure 7:
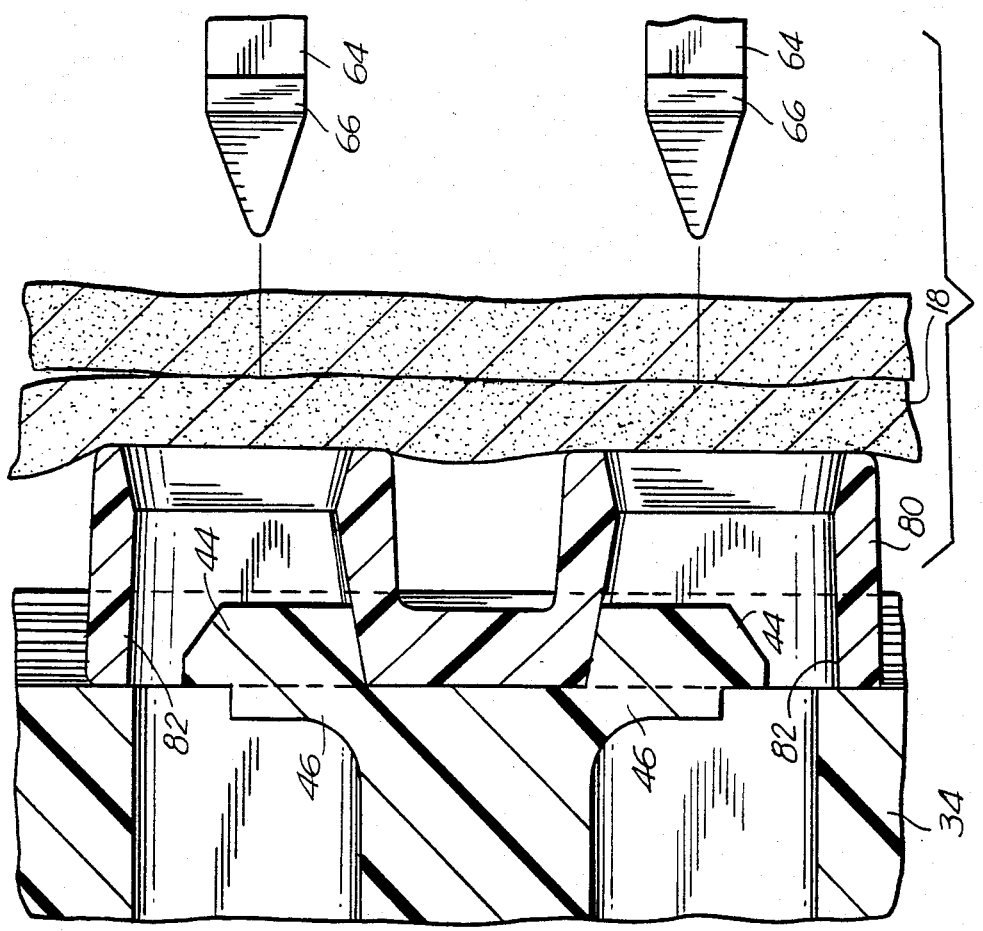
FIG. 7 is a sectional view taken along the line 7—7 in FIG. 6.
Figure 6:
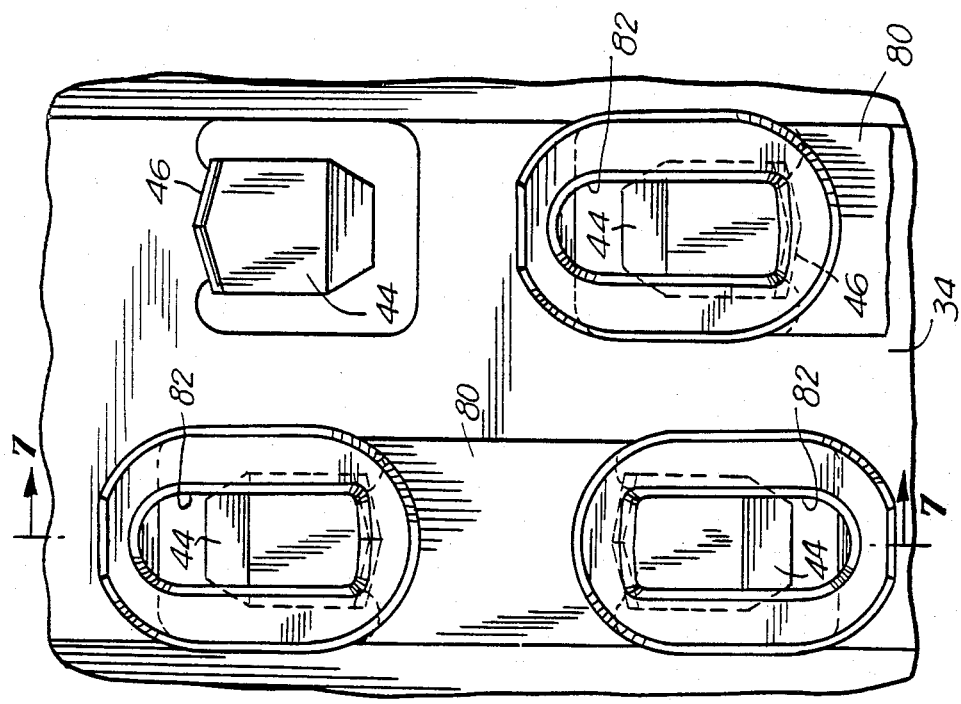
FIG. 6 is an enlarged elevational view of a portion of the apparatus of FIGS. 1-5.

Before surgical fasteners 60, 80 are applied to the tissue as described above, retainer parts 80 are held on retainer-holding assembly 34 by deformable holder members or lugs 44 (FIGS. 6 and 7) which project into the distal side of retainer part apertures 82. In their initial or first positions, lugs 44 fit tightly into apertures 82 so that retainer parts 80 are held securely on retainer-holding assembly 34 by the frictional fit between lugs 44 and the retainer parts. Like retainer parts 80, lugs 44 and the adjacent nondeformable supporting structure are preferably made of a plastic or plastic-like material. Most preferably, lugs 44 and the adjacent nondeformable supporting structure are integral.

Each lug 44 projects far enough into the associated retainer part aperture 82 so that, when the associated fastener prong 64 enters aperture 82, the distal end of the prong contacts the lug and deflects or deforms it to a second position as shown in FIGS. 8 and 9. In the embodiment shown in FIGS. 6-10, each lug 44 is basically a block which is connected along only one edge 46 to the nondeformable body of retainer-holding assembly 34. The other edges of each lug 44 are unsupported. Thus when the distal end of the associated prong 64 contacts each lug 44, the edge 46 of the lug by which it is connected to the body of retainer-holding assembly 34 acts as a deformable flexural hinge having a pivotal axis substantially perpendicular to the longitudinal axis of prong 64. Each lug 44 pivots about this hinge 46 when contacted by the distal end of the associated prong 64. Prongs 64 force lugs 44 substantially out of apertures 82, thereby breaking the frictional contact between lugs 44 and retainer parts 80. This releases retainer parts 80 from retainer-holding assembly 34 so that the fastened tissue is easily removed from the apparatus. Lugs 44 remain connected to the body of retainer-holding assembly 34 by hinges 46.

As mentioned above, two-part surgical fasteners of the type described herein are usually made of a plastic or plastic-like material. Such material may be preferred because it does not scatter X-rays the way metal surgical staples do. In some applications, however, it may not be possible for plastic prongs 64 to penetrate the tissue to be fastened unaided. If that is the case, metal piercers or guides may be provided in fastener-holder assembly 32 as shown, for example, in commonly-assigned, co-pending Green U.S. patent application Ser. No. 310,065, filed Oct. 9, 1981. In general, one such metal piercer is provided adjacent each prong. The sharp distal end of each piercer passes through the tissue just ahead of the distal end of the associated prong. If such piercers are used with the apparatus of the present invention, it will be apparent that the distal ends of the piercers rather than the distal ends of the fastener prongs may contact lugs 44 and deflect those lugs out of retainer part apertures 82. It will therefore be understood that the term "prong" as used herein and in the appended claims includes both the actual fastener part prong 64 and/or any associated metal piercer. This definition of the term "prong" applies even though the metal piercers may be withdrawn from proximity to the fasteners after the fastening has been completed.

When, as in the embodiment depicted in the accompanying drawing, multiple fasteners are driven simultaneously, especially without metal piercers or guides, it has been found desirable to connect pushers 50 rigidly together in a plurality of small groups which are mutually exclusive and collectively exhaustive of the totality of pushers. In the particularly preferred embodiment shown in FIG. 10, three pushers 50 are formed integrally on each pusher mounting 52. All of pusher mountings 52 are driven simultaneously by channel member 56 which is loosely associated with pusher mountings 52 so that channel member 56 does not constitute a rigid connection between pusher mountings 52. If each pusher 50 were separate, the pushers might have a tendency to become misaligned and therefore bind in their respective pusher channels 58. On the other hand, if all the pushers 50 were integral, any cocking of the pusher structure might again cause the pusher structure to bind relative to pusher channels 58. It has been found that joining pushers 50 together in small groups is preferable to either of the two extremes mentioned above. In particular, the integral structure of three pushers shown in FIG. 10 has been found especially desirable. This structure consists of two adjacent pushers 50 in one row of fasteners and one intermediate pusher 50 in the adjacent row of fasteners. The two pusher structures 52a and 52b adjacent to pusher structure 52 (portions of which are visible in FIG. 2) are identical but reversed (i.e., with two pushers 50 in the row of fasteners having only one pusher 50 in fully depicted pusher structure 52). Providing three pushers integrally in this manner helps to stabilize the individual pushers without introducing into the apparatus a long, rigid structure which might tend to bind even if slightly cocked.

It will be understood that the foregoing is merely illustrative of the principles of the invention, and that various modifications can be made by those skilled in the art without departing from the scope and spirit of the invention. For example, metal piercers can be provided to assist the fastener prongs in passing through the tissue if desired. As another example of modifications within the scope of the invention, actuator 10 and cartridge 30 could be made as one integral disposable unit.

I claim:

1. An apparatus for applying a surgical fastener made up of two interlocking parts comprising:
    a fastener including a fastener part having a prong which passes through the tissue to be fastened and a retainer part for interlocking with the end of the prong after it has passed through the tissue to prevent the prong from being subsequently withdrawn from the tissue; and
    a structure for releasably supporting the retainer part prior to interlocking of the prong and the retainer part, the supporting structure including a deformable part for releasably engaging the retainer part, the deformable part being contacted and deformed by the prong as the prong interlocks with the retainer part, and the deformable part responding to such deformation by releasing the retainer part.

2. The apparatus defined in claim 1 wherein the deformable part engages the retainer part by frictional contact between the deformable part and the retainer part.

3. The apparatus defined in claim 1 wherein the retainer part includes an aperture extending through the retainer part substantially parallel to the longitudinal axis of the prong, wherein, prior to deformation, the deformable part extends into the aperture from the side of the retainer part which faces away from the prong, and wherein the prong enters the aperture in order to interlock with the retainer member and to substantially displace the deformable part from the aperture.

4. The apparatus defined in claim 3 wherein the supporting structure further includes a retainer backup part adjacent the side of the retainer part which faces away from the prong, and wherein the deformable part comprises:
    a lug which, prior to deformation, extends into the aperture from the side of the retainer part which faces away from the prong; and
    a hinge connection between one side of the lug and the retainer backup part.

5. The apparatus defined in claim 4 wherein the pivotal axis of the hinge connection is substantially perpendicular to the longitudinal axis of the prong.

6. The apparatus defined in claim 4 wherein the lug is unsupported relative to the retainer backup part except for the hinge connection.

7. The apparatus defined in claim 4 wherein the retainer backup part, the lug, and the hinge connection are integral, and wherein the hinge connection is a flexural hinge.

8. An apparatus for applying a surgical fastener comprising:
    a fastener member located on one side of the tissue to be fastened and having a prong which passes through the tissue to be fastened;
    a retainer member located on the other side of the tissue to be fastened and having an aperture for receiving and retaining the end of the prong after it has passed through the tissue to prevent the prong from being subsequently withdrawn from the tissue;
    a structure adjacent the side of the retainer member which faces away from the tissue to be fastened for supporting the retainer member against the tissue prior to and during insertion of the prong in the aperture;
    a holder member for releasably engaging the retainer member and holding the retainer member against the supporting structure prior to insertion of the prong in the aperture;
    a deformable connection for connecting the holder member to the supporting structure; and
    means responsive to the insertion of the prong in the aperture for deforming the deformable connection so that the holder member moves out of engagement with the retainer member and permits the retainer member to move away from the supporting structure.

9. The apparatus defined in claim 8 wherein the holder member engages the retainer member by frictional contact with the retainer member.

10. The apparatus defined in claim 8 wherein the holder member is disposed in a portion of the retainer member aperture while engaging the retainer member, and wherein the prong forces the holder member out of the retainer member aperture when the prong enters the aperture.

11. The apparatus defined in claim 10 wherein the deformable connection is a hinge connection between one side of the holder member and the supporting structure.

12. The apparatus defined in claim 11 wherein the pivotal axis of the hinge connection is substantially perpendicular to the longitudinal axis of the prong.

13. The apparatus defined in claim 11 wherein the holder member is unsupported relative to the supporting structure except for the hinge connection.

14. The apparatus defined in claim 11 wherein the supporting structure, the holder member, and the hinge connection are integral, and wherein the hinge connection is a flexural hinge.

15. An apparatus for applying a surgical fastener made up of two interlocking parts comprising:
    a fastener including a fastener part having a prong which passes through the tissue to be fastened and a retainer part for interlocking with the end of the prong after it has passed through the tissue to prevent the prong from being subsequently withdrawn from the tissue;
    a first member for supporting the retainer part prior to interlocking of the prong and the retainer part; and
    a second member connected to the first member and movable between a first position in which the second member engages the retainer part to secure the retainer part to the first member, and a second position in which the second member releases the retainer part so that the retainer part is no longer secured to the first member, the second member being contacted and moved from the first position to the second position by the prong as the prong interlocks with the retainer part.

16. The apparatus defined in claim 15 wherein the retainer part includes an aperture extending through the retainer part substantially parallel to the longitudinal axis of the prong, wherein in the first position the second member extends into the aperture from the side of the retainer part which faces away from the prong, and wherein the prong enters the aperture in order to interlock with the retainer member and to substantially displace the second member from the aperture which corresponds to the second position of the prong.

17. The apparatus defined in claim 16 wherein the second member engages the retainer part by frictional contact with interior surfaces of the aperture.

18. The apparatus defined in claim 17 wherein the second member is pivotally connected to the first member by a hinge connection along a first side of the second member, the pivotal axis of the hinge connection being substantially perpendicular to the longitudinal axis of the prong.

19. The apparatus defined in claim 18 wherein the first member, the second member, and the hinge connection are integral.

20. The apparatus defined in claim 19 wherein the hinge connection is a flexural hinge.

21. Apparatus for simultaneously driving a plurality of surgical fasteners from a fastener-holding assembly, each fastener including a longitudinal base substantially parallel to the surface of the tissue to be fastened and two prongs substantially perpendicular to the surface of the tissue to be fastened, each prong being attached to the base adjacent a respective one of the ends of the base, the fasteners being disposed in two parallel rows which are longitudinally offset from one another, the apparatus comprising:

a plurality of fastener pushers disposed in a fastener-holding assembly, each pusher being substantially perpendicular to the surface of the tissue to be fastened and each pusher acting on the base of a respective one of the fasteners to drive the associated fastener from the fastener-holding assembly;

pusher mounting means for rigidly connecting adjacent pushers together in a plurality of groups which are mutually exclusive and collectively exhaustive of the totality of pushers, each group of pushers consisting of two pushers respectively associated with two adjacent fasteners in one of the rows and one pusher associated with the intermediate fastener in the other row;

means for simultaneously pushing all of the groups of pushers toward the fasteners to drive the fasteners from the fastener-holding assembly; and each pusher mounting means being located adjacent another pusher mounting means and having recessed shoulder portions retaining the rows of pushers in alignment without forming a rigid connection between any of said groups.

* * * * *